United States Patent [19]

Kluger et al.

[11] 4,153,567
[45] May 8, 1979

[54] ADDITIVES FOR LUBRICANTS AND FUELS

[75] Inventors: Edward W. Kluger, Pauline; John W. Miley, Inman; Tien K. Su, Spartanburg, all of S.C.

[73] Assignee: Milliken Research Corporation, Spartanburg, S.C.

[21] Appl. No.: 850,457

[22] Filed: Nov. 10, 1977

[51] Int. Cl.² .................... C10M 1/32; C10L 1/22; C07D 207/24; C07D 209/32
[52] U.S. Cl. .................... 252/51.5 A; 44/71; 260/326.5 F; 260/326.5 FM
[58] Field of Search .................... 252/51.5 A; 44/71; 260/326.5 F, 326.5 FM

[56] References Cited

U.S. PATENT DOCUMENTS

| | | | |
|---|---|---|---|
| 3,272,746 | 9/1966 | Le Suer et al. | 252/47.5 |
| 3,449,250 | 6/1969 | Fields | 252/51.5 A |
| 3,620,977 | 11/1971 | Honnen et al. | 252/51.5 A |
| 3,697,428 | 10/1972 | Meinhardt et al. | 252/56 D |
| 3,804,763 | 4/1974 | Meinhardt | 252/51.5 A |
| 3,951,977 | 4/1976 | Plasek et al. | 252/51.5 A |
| 4,044,033 | 8/1977 | Fusco | 260/410 |
| 4,071,548 | 1/1978 | Okamoto | 252/51.5 A |
| 4,077,992 | 3/1978 | Fusco | 252/56 S |

Primary Examiner—Delbert E. Gantz
Assistant Examiner—Irving Vaughn
Attorney, Agent, or Firm—H. William Petry

[57] ABSTRACT

Additives for lubricants and fuels having the general structure

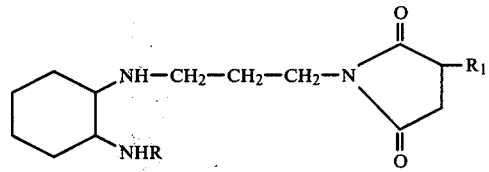

wherein R is H, —CH₂CH₂CH₂NH₂ or

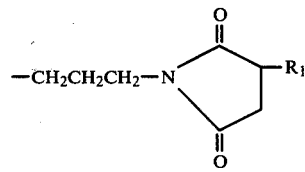

and $R_1$ is an alkyl moiety containing at least about 8 carbon atoms or a substantially saturated olefin polymer having an average molecular weight of from about 200 to about 5000. Polyamino substituted cycloaliphatic compounds simultaneously treated with at least one olefin polymer substituted succinic anhydride or at least one alkyl substituted succinic anhydride in which the alkyl moiety contains at least about 8 carbon atoms produce such oil-dispersible compositions.

11 Claims, No Drawings

ADDITIVES FOR LUBRICANTS AND FUELS

This invention relates to novel lubricant and fuel additives. In one aspect it relates to dispersants for lubricant and fuel compositions. In particular, the invention relates to additives for lubricant and fuel compositions prepared by reacting certain carboxylic acid acylating agents with a polyamino substituted cycloaliphatic compound.

The major problem associated with crank case lubricants employed in internal combustion engines is the presence in the lubricant of foreign particles, such as dirt, soot, water and decomposition products resulting from a breakdown of the lubricating oil. Similarly, problems are encountered with the presence of foreign materials in the fuel burned in the internal combustion engine. In order to prevent a buildup of sludge or other undesirable constituents within the lubricating oil, or fuel, it is necessary that such foreign particles be maintained in suspension within the lubricating oil or fuel so that such can readily be removed or passed through the internal combustion engine without a buildup of such foreign matter within the lubricating oil or the fuel tank. Numerous additives have heretofore been proposed to prevent the buildup of sludge and particulate matter within the crank case oil of the internal combustion engine or within the fuel tank supplying the fuel to the internal combustion engine. For example, to obviate the problem or reduce the problem, the approach has generally been by employing either known detergents, such as metal phenates and sulfonates, or oil-soluble nitrogen-containing compositions. Many of the prior art additives are the reaction products of relatively high molecular weight carboxylic acid acylating agents and certain specified amines, alcohols, and combinations of alcohols. However, problems have been encountered in providing additives which are stable and functional to suspend the foreign material in both the lubricating oil and the fuel, not only at high temperatures, but also at low temperatures. Thus, new and improved dispersants for lubricants and fuels are constantly being sought.

Therefore, an object of the invention is to provide novel compositions of matter.

Another object of the invention is to provide compositions which are adapted for use as additives in hydrocarbon oils and fuels for internal combustion engines.

These and other objects, advantages, and features of the present invention will become apparent to those skilled in the art from a reading of the following detailed description.

According to the present invention, we have an improved fuel and lubricant additive compositions produced by the process comprising simultaneously reacting a polyamine substituted cycloaliphatic compound having the general structure

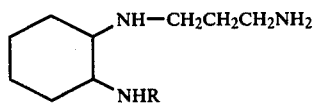

wherein R is hydrogen or $CH_2CH_2CH_2NH_2$, with at least one substituted aliphatic polycarboxylic acid acylating agent selected from the group consisting of carboxylic acids and their corresponding halides, anhydrides, and esters, said carboxylic acid acylating agents having at least 12 carbon atoms per molecule. More specifically, the novel oil-dispersible and/or oil-soluble additives have the general structure

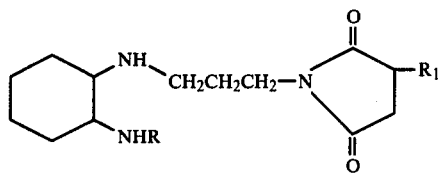

wherein R is H, $—CH_2CH_2CH_2NH_2$ or

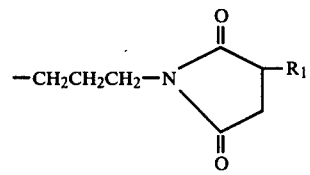

and $R_1$ is an alkyl moiety containing at least about 8 carbon atoms or a substantially saturated olefin polymer having an average molecular weight of from about 200 to about 5000.

The compositions of this invention are useful as dispersing agents in lubricants and fuels, especially fuels employed in internal combustion engines and lubricants intended for use in the crank case of internal combustion engines, gears, and power transmitting units. However, it is to be understood that such dispersing agents should also be useful in other systems employing lubricants where it is desirable that foreign matter, such as dirt, soot, water, and the like may be present and it is desirable to maintain such foreign matter in a suspended state within the lubricating oil.

The polyamine substituted cycloaliphatic compounds having the general structure

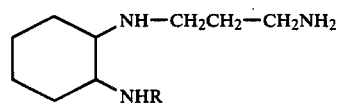

wherein R is H or $CH_2CH_2CH_2NH_2$ which are reacted with a polycarboxylic acid acylating agent to produce the novel fuel and lubricant additives of the present invention can readily be prepared by cyanoethylation of 1,2-diaminocyclohexane to produce the cyanoethylated 1,2-diaminocyclohexane which can be reduced with ammonia to provide the amine derivative. To illustrate the preparation of such polyamine cycloaliphatic compounds, the following series of reactions are presented.

PREPARATION OF POLYAMINE CYCLOALIPHATIC COMPOUNDS 1,2-Diaminocyclohexane (1) is cyanoethylated with acrylonitrile in the presence of an acid catalyst (Equation 1). With one mole

EQUATION 1

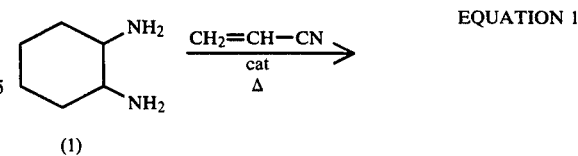

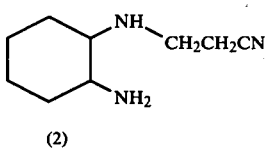

(2)

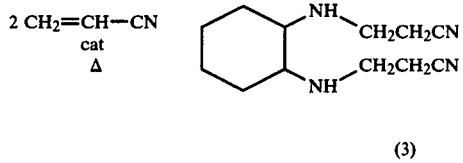

(3)

of acrylonitrile the monocyanoethylated product, N-(2-cyanoethyl)-1,2-diaminocyclohexane, (2) is formed, whereas two moles of acrylonitrile react to give the dicyanoethylated product, N,N'-di-(2-cyanoethyl)-1,2-diaminocyclohexane, (3).

The crude reaction mixtures can be separated by any suitable means, such as distillation under vacuum. Any suitable acid catalyst can be employed. Typical of such catalyst are p-toluene-sulfonic acid and acetic acid salts. Generally, the above reaction is carried out at a temperature of from about 20° C. to about 100° C.

The above-described cyanoethylated-1,2-diaminocyclohexane can be reduced with hydrogen in the presence of ammonia, such as methyl alcohol; N-(2-cyanoethyl)-1,2-diaminocyclohexane, (2), can be reduced to give a triamine, N-(3-aminopropyl)-1,2-diaminocyclohexane, (4), while N,N'-di(2-cyanoethyl)-1,2-diaminocyclohexane, (3), can be reduced to give tetramine, N,N'-di-(3-aminopropyl)-1,2-diaminocyclohexane, (5).

EQUATION 2

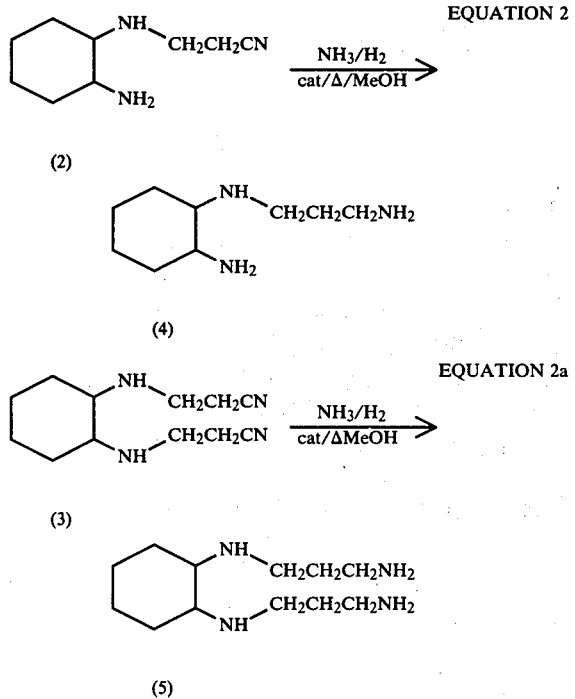

Any suitable reduction catalyst can be employed. Typical of such reduction catalyst are Raney nickel, iron, palladium, platinum, ruthenium, cobalt, rhodium, osmium, iridium, including salts, and oxides thereof, and the like. Further, such catalysts can be extended on a support, such as charcoal, aluminum, kieselguhr and the like.

The crude reaction mixture can then be separated by any suitable means, such as by distillation under vacuum.

The above-described polyamine substituted cycloaliphatic compound is then reacted with a suitable polycarboxylic acid acylating agent to produce the desired fuel and lubricant additives having the structure

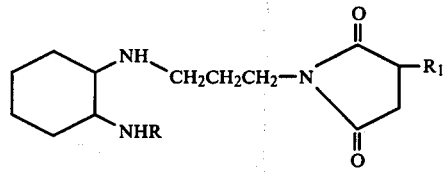

wherein R is H, —CH$_2$CH$_2$CH$_2$NH$_2$ or

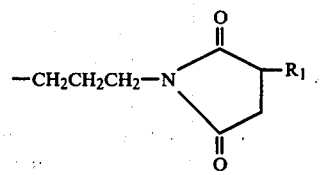

and R$_1$ is an alkyl moiety containing at least about 8 carbon atoms or a substantially saturated olefin polymer having an average molecular weight of from about 200 to about 5000.

The reaction between the polyamine substituted cycloaliphatic compound and the polycarboxylic acid acylating agent is generally exothermic. However, after the initial exothermic reaction between such compounds have been achieved, it is desirable that the reaction mixture be heated to a temperature effective to remove water therefrom equivalent to the number of moles of

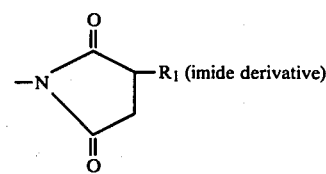

present in the final composition. Removal of water is necessary in order to allow the imide ring to be formed. While the temperature at which the reaction mixture is heated can vary widely, such is generally carried out at a temperature in the range of from about 95° C. to about 150° C. Of course, if one were to include an azeotrope agent within the liquid admixture, the temperature required to remove the water could be substantially lowered.

The polycarboxylic acid acylating agent employed in the reaction with the polyamine substituted cycloaliphatic compound to produce the desired novel fuel and lubricant additives of the present invention can be any suitable carboxylic acid, or its corresponding halides, anhydrides and esters.

The substantially saturated aliphatic hydrocarbon substituted succinic acid anhydrides are essentially desirable as acylating agents in the preparation of the novel fuel and lubricant additives of the present invention. These succinic acid anhydride acylating agents are readily prepared by reacting maleic anhydride with a chlorinated polyolefin or an olefin containing at least about 8 carbon atoms. The reaction between the two constituents to provide the substantially saturated aliphatic hydrocarbon substituted succinic acids and anhydrides is accomplished by heating the reaction mixture at a temperature of about 100° C. to about 300° C. for a period of time effective to allow the reaction to proceed. The product from such a reaction is a substituted succinic anhydride having an alkyl moiety or a substantially saturated olefin polymer moiety. In producing the desired oil-dispersible and/or soluble additives of the present invention, the particular olefin constituent or chlorinated polyolefin constituent should be selected to insure that the alkyl moiety of the substituted succinic anhydride contains at least about 8 carbon atoms, preferably from about 8 to about 150 carbon atoms, or that the substantially saturated olefin polymer moiety of such substituted succinic anhydride has an average weight of from about 200 to about 5000. Thus, the polymerized 1-monoolefin-substituted succinic anhydride will have an average molecular weight of from about 300 to about 5100.

In order to further illustrate the subject of the present invention, the following examples are given. Such examples are given for illustrative purposes only and are not to be construed as unduly limiting the scope of the subject invention. Unless otherwise indicated, all percentages and parts used in the following examples and elsewhere in the specification and claims represent percent by weight and parts by weight.

EXAMPLE 1

In a 250cc three-necked flask equipped with a magnetic stir bar, Dean Stark trap, and heating mantle was placed 21.9 gm (0.08 mole) of dodecencylsuccinic anhydride which had been dissolved in 50 cc of toluene. To this solution was added 18.2 gm (0.08 mole) of tetramine, N,N'-di(-3-aminopropyl)-1,2-diaminocyclohexane,

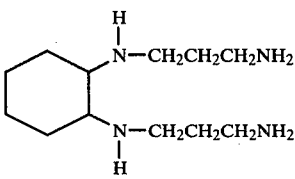

which also had been dissolved in 50 cc of toluene. An exothermic reaction occurred on mixing. The reaction mixture was then refluxed for 6 hours and water was collected in the Dean Stark trap. The toluene was removed by evaporation to give 99.3% yield of the crude viscous adduct. An infrared spectrum indicated that no anhydride was present. The compound produced from the above reaction can be represented structurally as

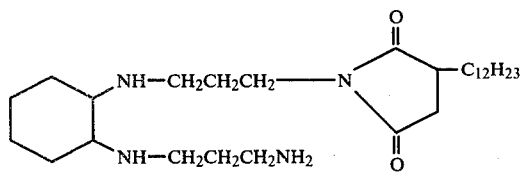

EXAMPLE 2

In a 250 cc three-necked flask equipped with a magnetic stir bar, Dean Stark trap, and heating mantle was placed 31 gm (0.087 mole) of alkenylsuccinic anhydride having an average molecular weight of 356 in 50 cc of toluene. To this solution was added 19.9 gm (0.087 mole) of the tetramine, e.g. N,N'-di-(3-aminopropyl)-1,2-diaminocyclohexane.

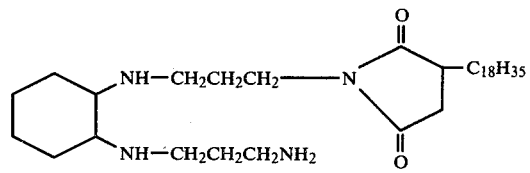

An exothermic reaction occurred on mixing the solutions. The reaction mixture was then refluxed for 14 hours and the resulting water was collected in the Dean Stark trap. The toluene was removed by evaporation to give 97% yield of the crude viscous adduct. An infrared spectrum indicated that no anhydride was present. The compound produced from the above reaction can be represented structurally as

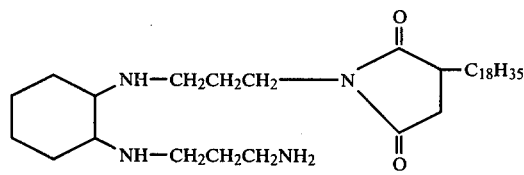

EXAMPLE 3

To mineral oil with viscosity of 22 centipoise at 23° C., the alkyenylsuccinic anhydride tetramine adduct (product produced in Example 2) was introduced to make a mixture at room temperature. This adduct was completely dissolved in the mineral oil at 1% and partially dissolved in it above 5%. The infrared spectrum of the mineral oil rich phase shows the new absorption bands at 1700cm$^{-1}$ and 1700cm$^{-1}$. This indicates that this particular adduct (imide structure) is miscible with mineral oil in amounts of up to about 5 percent.

EXAMPLE 4

To mineral oil with a viscosity of 22 centipoise at 23° C., the dodecenylsuccinic anhydride tetramine adduct (product produced in Example 1) was added to prepare a mixture at room temperature. This adduct was soluble in the mineral oil phase in a new amount of up to about 1% by weight. The infrared spectrum of the mineral oil rich phase also shows the new appearance of the absorption bands at 177 cm$^{-1}$ and 1700cm$^{-1}$ which corresponds to the adduct (imide group). It can be concluded that this particular adduct is soluble in mineral oil in amounts up to about 1 weight percent.

EXAMPLE 5

One-tenth gram of carbon black having a particle size of 24mu was introduced into 10 grams of mineral oil solution contains 0% and 1% of the product produced in Example 2. After mixing thoroughly, these oil mixtures were each placed in a transparent centrifuge tube and centrifuged for 1 minute at the speed of 3000 rpm. The oil-carbon black mixture became almost substantially clear with the precipitation of carbon black in the bottom; but the mineral oil-carbon black admixture of the product of Example 2 appeared to have a uniform dispersion of carbon black.

EXAMPLE 6

One-tenth gram of carbon black having a particle size of 24mm was added to 10 grams of oil solution with 0% and 1% of the product produced in Example 1. After mixing and centrifuging as set forth in Example 5, the mineral oil-carbon black mixture containing none of the product of Example 1 solution with the precipitation of carbon black in the bottom, but the oil solution with 1% adduct still contained dispersed carbon black.

EXAMPLE 7

A series of admixtures were formulated using varying amounts of the product produced in Example 2 and a mineral oil having a kinematic viscosity of 7.7 centistokes at 100° F. Each admixture contained a total weight of 80 grams. Into each admixture was added 1 gram of carbon black having a particle size of 24 mm and 15 grams of glass beads. Each admixture, which had been placed in a transparent container, was shaken using a Red Devil paint mixer for 10 minutes and thereafter centrifuged for 30 seconds at a speed of 3000rpm. Each admixture was then removed from the centrifuge and the admixtures were evaluated to determine the effect of the product of Example 2 as an oil dispersant. Tabulated on the following page are the results of such experiments.

Table

| % of Product of Example 2 in Oil | Observation of Carbon Black in Oil |
| --- | --- |
| 0 | Substantially complete precipitation of carbon black |
| 0.01 | Substantially complete precipitation of carbon black |
| 0.10 | Partial precipitation of carbon black |
| 1.00 | Substantially uniform dispersion of carbon black in oil, e.g., substantially no carbon black precipitation |

The above examples clearly indicate the preparation of the novel lubricant and fuel additives of the present invention. Further, the data clearly indicates that such compounds can effectively disperse carbon black in mineral oil, and thus would indicate that such compounds have the desired dispersing properties for use as dispersing agents. Further, the solubility of such compounds in the mineral oil is indicative of their use as a lubricating or fuel dispersing agent or additive.

Having thus described the invention, we claim:

1. A fuel and lubricant additive produced by the process comprising simultaneously reacting substantially equal molar amounts of a polyamine substituted cycloaliphatic compound having the general structure

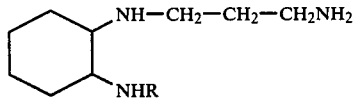

wherein R is H or —CH$_2$CH$_2$CH$_2$NH$_2$ with a substituted aliphatic polycarboxylic acid anhydride acylating agent said polycarboxylic acid anhydride acylating agent containing at least about 12 carbon atoms, at a temperature and for a period of time effective to remove from the reaction mixture an amount of water equivalent to the number of moles of an imide derivative moiety having the general structure

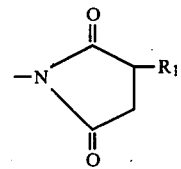

present in said addtive, R$_1$ of said imide derivative moiety being an alkyl moiety containing at least about 8 carbon atoms or a substantially saturated olefin polymer having an average molecular weight of from 200 to about 5000.

2. The fuel and lubricant additive produced by the process of claim 1 wherein said polyamine substituted cycloaliphatic compound is

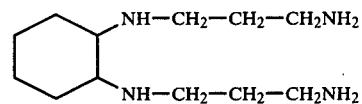

3. The fuel and lubricant additive produced according to the process of claim 2 wherein said substituted aliphatic polycarboxylic acid anhydride alkylating agent is an alkyl substituted succinic acid anhydride.

4. The fuel and lubricant additive produced according to the process of claim 3 wherein the alkyl moiety contains from about 8 to about 150 carbon atoms.

5. The fuel and lubricant additive produced according to the process of claim 2 wherein said substituted aliphatic polycarboxylic acid anhydride alkylating agent is a substantially saturated olefin polymer substituted succinic acid anhydride in which the polymer constituent has an average molecular weight of from about 200 to about 5000.

6. A novel lubricant and fuel additive having the general structure

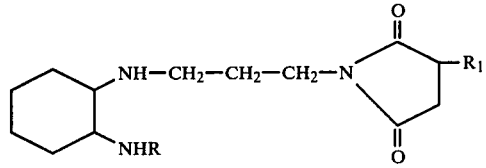

wherein R is H, —CH$_2$CH$_2$CH$_2$NH$_2$ or

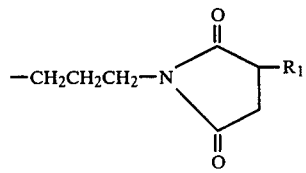

and R$_1$ is an alkyl moiety containing at least about 8 carbon atoms or a substantially saturated olefin polymer having an average molecular weight of from about 200 to about 5000.

7. The lubricant and fuel additive of claim 6 wherein R is H and R$_1$ is an alkyl moiety containing from about 8 to 150 carbon atoms.

8. The lubricant and fuel additive of claim 6 wherein R is H and R$_1$ is a polymerized (lower 1-monoolefin)

constituent having a molecular weight of from about 200 to about 5000.

9. A composition comprising a major portion of a lubricant or fuel and a minor effective amount of a dispersant having the general structure

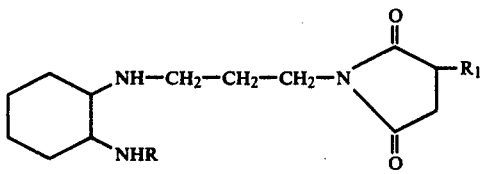

wherein R is H, —CH$_2$CH$_2$CH$_2$NH$_2$ or

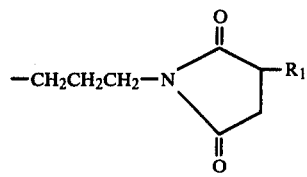

and R$_1$ is an alkyl moiety containing at least about 8 carbon atoms or a substantially saturated olefin polymer having an average molecular weight of from about 200 to about 5000.

10. The composition of claim 9 wherein R of said dispersant is H and R$_1$ is an alkyl moiety containing from about 8 to 150 carbon atoms.

11. The composition of claim 9 wherein R of said dispersant is H and R$_1$ is a polymerized (lower 1-monoolefin) constituent having a molecular weight of from about 200 to about 5000.

* * * * *